US008464722B2

(12) United States Patent
Chua

(10) Patent No.: US 8,464,722 B2
(45) Date of Patent: Jun. 18, 2013

(54) FOLDED TELESCOPIC EQUIPMENT DRAPE AND METHOD OF FOLDING AND USING THE SAME

(75) Inventor: Mark Spencer G. Chua, Glenview, IL (US)

(73) Assignee: Medline Industries, Inc., Mundelein, IL (US)

( * ) Notice: Subject to any disclaimer, the term of this patent is extended or adjusted under 35 U.S.C. 154(b) by 454 days.

(21) Appl. No.: 12/717,704

(22) Filed: Mar. 4, 2010

(65) Prior Publication Data

US 2011/0214679 A1    Sep. 8, 2011

(51) Int. Cl.
*A61B 19/08* (2006.01)
(52) U.S. Cl.
USPC .......................................... 128/855
(58) Field of Classification Search
USPC ....... 128/849, 855, 856; 378/204, 210; 2/239, 2/114
See application file for complete search history.

(56) References Cited

U.S. PATENT DOCUMENTS

| | | | |
|---|---|---|---|
| 3,025,957 A | | 3/1962 | Wall et al. |
| 3,540,441 A * | | 11/1970 | Collins ............ 128/855 |
| 3,707,964 A * | | 1/1973 | Patience et al. ........... 128/856 |
| 3,835,851 A * | | 9/1974 | Villari ............ 128/853 |
| 3,881,476 A | | 5/1975 | Bolker et al. |
| 3,952,738 A * | | 4/1976 | Krzewinski ............ 128/855 |
| 3,955,569 A * | | 5/1976 | Krzewinski et al. ........ 128/855 |
| 3,998,221 A * | | 12/1976 | Collins ............ 128/855 |
| 4,627,427 A | | 12/1986 | Acro |
| 5,197,493 A * | | 3/1993 | Grier-Idris ............ 128/853 |
| 5,490,524 A * | | 2/1996 | Williams et al. ............ 128/849 |
| 6,405,730 B2 * | | 6/2002 | Levitt et al. ............ 128/849 |
| 6,497,233 B1 * | | 12/2002 | DeAngelis ............ 128/849 |
| 2007/0175486 A1 | | 8/2007 | Bogojevik et al. |
| 2008/0006278 A1 * | | 1/2008 | Henke-Sarmento et al. . 128/849 |
| 2011/0214679 A1 | | 9/2011 | Chua |

FOREIGN PATENT DOCUMENTS

WO    WO-2008/060364    5/2008

OTHER PUBLICATIONS

Medline Industries, Inc., "Drape, C-Arm, Mobile Xray", https://www.medline.com/b2b/load_catalog.do, Published prior to filing of the present application,(Unknown Pub. Date).
3M, Inc., "Steri-Drape.TM C-Arm Drapes", http://solutions.3m.com/wps/portal/3M/en_US/IP/infectionprevention/solutions/sterile-field-surface/drapes/?PC_7_RJH9U5230GE3E02LECFTDQUD6_nid=GSSYGBPFYWbe88CZN1GGVJgI, Published prior to filing of the present application,(Unknown Pub. Date).

(Continued)

*Primary Examiner* — Patricia Bianco
*Assistant Examiner* — Raymond E Harris
(74) *Attorney, Agent, or Firm* — David Noskowicz; Philip H. Burrus, IV

(57) ABSTRACT

An equipment drape (1000) is made from an elongated drape body (1401) that includes an equipment opening (1041). The elongated drape body (1401) is telescopically folded (1403) to form a telescopic drape body (1404). An accordion fold (1501) is then applied to form a rectangular shape (1503). The distal edges (1011,1012) are then folded back over the rectangular shape (1503) to meet at a longitudinal part (1511). Insertion indicators (1043,1044) can be attached to the equipment opening (1041). A user can easily and quickly insert their hands into the equipment opening (1041) to deploy the equipment drape (1000) with a single motion without having to first fumble with and unfold the drape.

20 Claims, 9 Drawing Sheets

OTHER PUBLICATIONS

GE Healthacre, "C-Arm Drapes", http://www.gehealthcare.com/usen/xr/surgery/docs/SurgeryDrapes&Film.pdf, Published prior to filing of present application,(Unknown Pub. Date).

Choi, Seok K., "PCT Search Report", PCT/US2012/059492; Filed Oct. 10, 2012; Mailed Mar. 18, 2013.

* cited by examiner

FOLDED TELESCOPIC EQUIPMENT DRAPE AND METHOD OF FOLDING AND USING THE SAME

BACKGROUND

1. Technical Field

This invention relates generally to covers for equipment, and more particularly to a folded, telescopic drape for medical equipment, as well as a method for folding and using the same.

2. Background Art

In clinical environments, such as hospitals, medical offices, and ambulatory surgical centers, a wide range of equipment is used to perform diagnostics and procedures. This equipment can include devices like C-arm image devices, ultrasound probes, microscopes, and radiographic equipment. This equipment is expensive and must be protected during use. For example, medical professionals must ensure that this valuable equipment is not exposed to surgical fluids or other contaminants. Additionally, medical professionals using the equipment must ensure that the sterile field is protected, i.e., that patients are not inadvertently contaminated due to microbes or other matter disposed on the equipment.

To solve this need equipment drapes have been developed. These equipment drapes are often thin layers of translucent plastic that pass over and about a piece of equipment. They can resemble large plastic bags that have been fitted generally in shape to the equipment they are intended to protect.

For small pieces of equipment, such as handheld tools, the equipment drapes are easily managed. However, for large pieces of equipment, such as C-arm imagers, the drapes are large and unwieldy. Consequently, these drapes are folded many times so that they fit into a relatively manageable package.

The problem with prior art folding techniques is two-fold. First, since the drapes are generally transparent, it is often very difficult to find the ends of the drape. One must sometimes rummage along the surface of the drape until an end is found, which results in a drape that has been carelessly unfolded and is consequently difficult to put on the machine. Second, prior art drapes include a large number of folds. This large number of folds is time consuming and cumbersome to open. The time of medical professionals in a procedure room is valuable.

There is thus a need for an improved equipment drape that is simpler and quicker to transfer from package to machine.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
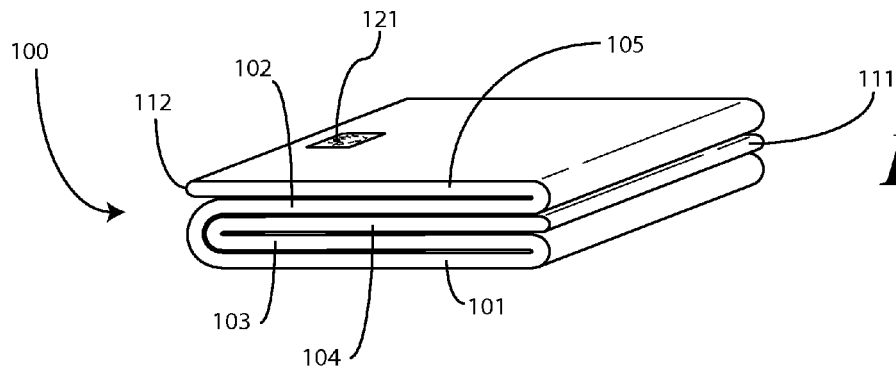
FIGS. 1-6 illustrate a prior art equipment drape at various stages of deployment.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the present invention provide an equipment drape that is simpler to unfold and quicker to apply than are prior art drapes. The ease and efficiency with which embodiments of the present invention can be used is due in part to the way that embodiments of the present invention are folded. While some prior art drapes took six or more steps or mechanical manipulations, embodiments of the present invention can be put into use with as little as three steps—a fifty-percent increase in efficiency.

While medical applications will be used herein for illustrative purposes and simplicity of discussion, it will be clear to those of ordinary skill in the art having the benefit of this disclosure that applications for embodiments of the present invention are not so limited. Embodiments of the present invention can be used in any application where a relatively large piece of equipment needs to be covered by a disposable drape. Using a medical example, embodiments of the present invention can be conveniently stored in an operating room and then quickly and easily opened and applied to equipment so as to cover it and preserve the integrity of the sterile field. Embodiments of the present invention are well suited for use with large pieces of equipment such as C-arm imagers and surgical microscopes.

In prior art drapes, as will be shown below in FIGS. 1-6, it is often very difficult to find the proper opening in the drape when unfolding. Prior art drapes often include numerous stickers and indication that are confusing. For example, some prior art drapes include stickers with little pictures of hands on them. However, there can be three, four, or more such pictures. Some pictures are for initially unfolding the drape, while others are to be used when extending the drape over the equipment. This abundance of indicators can be confusing. Further, due to the way prior art drapes are folded, it can take several unfolding steps to even reveal a sticker for viewing. It also takes multiple unfolding steps to begin to reveal the proper opening into which the hands are to be inserted. Due to this large number of folds and stickers, as well as the difficulty that can occur finding a sticker or hand insertion point, it can take relatively large amount of time to apply the drape.

Another problem with prior art drapes is their effect on the sterile field. As most prior art drapes can take six or more motions to open, there is a high risk that the sterile field about the machine will be contaminated. Two reduce the risk of contaminating the sterile field, some medical service providers will actually require two people to open prior art drapes to ensure that the integrity of the sterile field is maintained.

Embodiments of the present invention resolve these issues by providing a drape that dramatically reduces the amount of time and steps required to deploy the drape. Embodiments of the present invention require only a single user for deployment and significantly reduce the risk of contaminating the sterile field when deploying the drape. With embodiments of the present invention, a user may actually insert their hands into an opening in the drape prior to unfolding.

In one embodiment of the invention, a telescopically folded drape is given an accordion fold so as to resemble a rectangle when placed on a horizontal surface. Distal ends of the rectangle are folded back across the drape to meet at a longitudinal part. The remaining drape structure is then folded beneath the longitudinal part in a direction opposite the folds made when folding the distal ends back across the drape. The resulting structure places the longitudinal part on one edge of the drape with an equipment opening disposed at a second edge. The user simply inserts hands into the equipment opening and makes an outward spreading motion to unfold the drape in a single, sweeping motion. As the user continues to push the hands into the initial opening, the telescopic fold then begins to unfurl.

In one embodiment, one or more insertion indicators are attached to the drape at the equipment opening. These equipment indicators extend from the folded drape and are easily visible even when the drape is completely folded. In one embodiment, two or fewer indicators are configured as tags having arrows disposed thereon. By using two or fewer indicators, with easy to understand directional arrows printed thereon, a user is instantly able to understand both where and in which direction the hands are to be inserted. Further, no unfolding steps are required to view the insertion indicators. The insertion indicators can be configured as paper, or another similar material, with removable adhesive being used to attach the indicators to the drape.

In one embodiment, an adhesive layer, such as a removable adhesive tape layer, is attached to each of the distal ends that are folded back upon the drape. The adhesive layer prevents the drape from becoming unfolded prior to use. Further, a perforation can be added to the adhesive layer to make separation even easier.

Turning now to FIG. 1, illustrated therein is one embodiment of a prior art equipment drape 100. The prior art equipment drape 100 is folded in a multi-layer sandwich configuration that includes a first portion 101 and second portion 102 wrapping about a third portion 103 and a fourth portion 104. Said differently, the third portion 103 and fourth portion 104 are "sandwiched" between the first portion 101 and second portion 102. Consequently, the fourth portion 104, which terminates in a first graspable end 111, cannot be accessed until the second portion 102 is unfolded from above.

However, to unfold the second portion 102, one must first grasp a second graspable end 112. The second graspable end 112 terminates a fifth portion 105 that is folded back across the fourth portion 104. In the embodiment of FIG. 1, a first sticker 121 having a hand printed thereon is shown. This hand is intended to instruct the user to initially grasp the second graspable end 112 first to deploy the prior art equipment drape 100.

Thus, to access the first graspable end 111, one must first grasp the second graspable end 112, unfold the fifth portion 105, and pull the fifth portion 105 back across the second portion 102, thereby unfolding the second portion 102 and exposing the fourth portion 104. Such a process is shown in FIG. 2.

Figure 2:
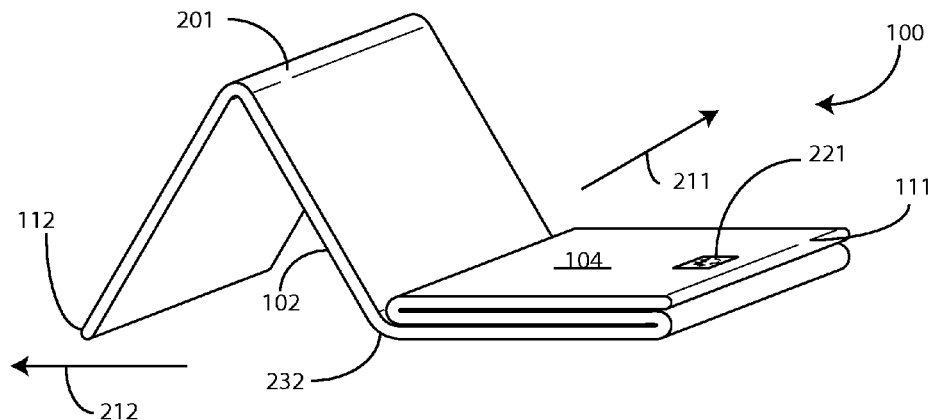

Turning now to FIG. 2, illustrated therein is the equipment drape of FIG. 1. In FIG. 2, the first three steps required for deploying the drape are completed or in progress. Specifically, a user has grasped the second graspable end 112 and has lifted it in a first direction 211, thereby unfolding a first fold 201. The user has then pulled the second graspable end 112 in a second direction 212, back across the second portion 102, thereby unfolding a second fold 232 and exposing the fourth portion 104.

Note that a second sticker 221 is now revealed. The second sticker 221 is intended to instruct the user to grasp the first graspable end 111. However, this second sticker 221 was not visible until the motions shown in FIG. 2 were performed. Consequently, a misunderstanding of the first sticker (121) would result in a user who was unaware that the first graspable end 111 should be grasped. Such a situation could result in an extended portion of the prior art equipment drape 100 being dropped, thereby potentially compromising the sterile field.

Figure 3:
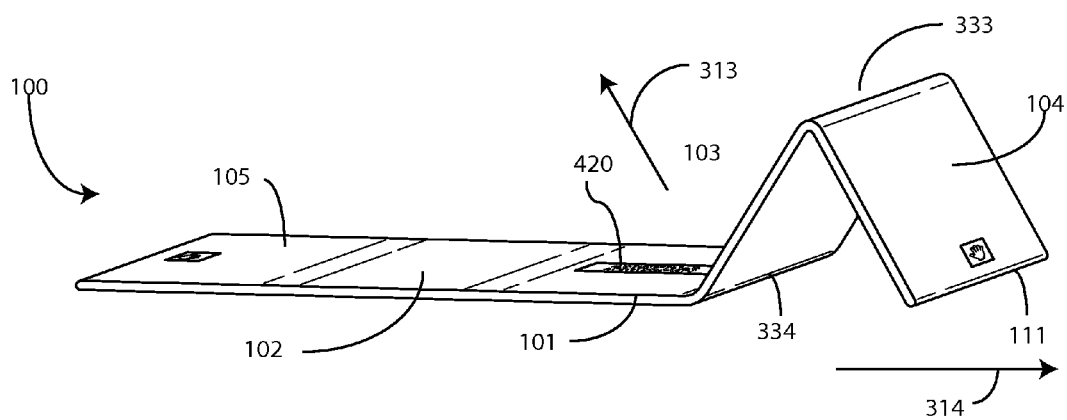

Turning now to FIG. 3, illustrated therein are more steps required to deploy the prior art equipment drape 100. Now that the fifth portion 105 and second portion 102 have been unfolded to reveal the fourth portion 104, a user has grasped the first graspable end 111 and has lifted it in a third direction 313, thereby unfolding a third fold 333. The user has then pulled the first graspable end 111 in a fourth direction 314, back across the third portion 103, thereby unfolding a fourth fold 334 and exposing the first portion 101. At this point, an instruction set 420 is revealed.

Figure 4:
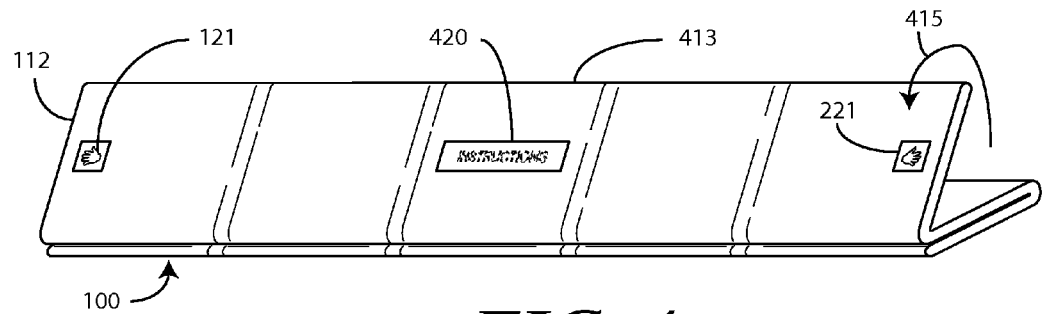

The user is now only partially done opening the prior art equipment drape 100. Turning now to FIG. 4, illustrated therein are more steps required to deploy the prior art equipment drape 100. The unfolding steps of FIGS. 2 and 3 have now revealed a third graspable end 413. While there is no hand sticker here, the user is apparently intuitively supposed to know to grasp the third graspable end 413 and pull it in a fifth direction 415, thereby temporarily obfuscating the instructions 420.

Figure 5:
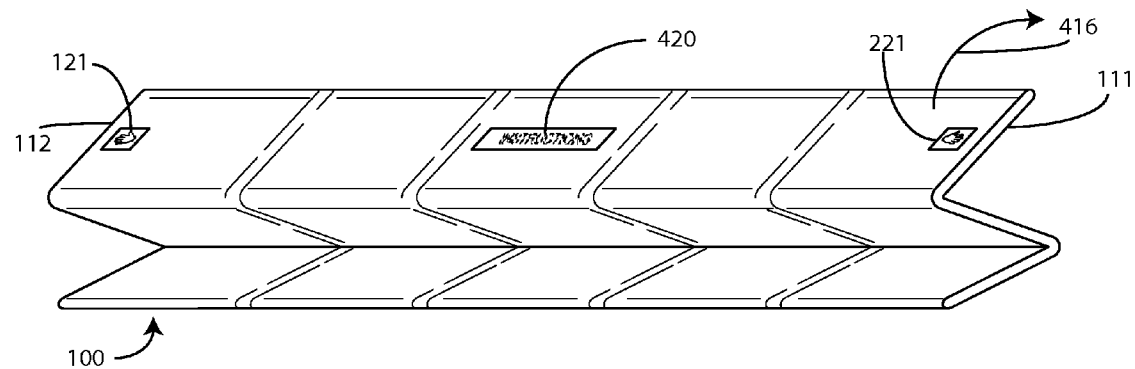

Turning now to FIG. 5, illustrated therein are more steps required to deploy the prior art equipment drape 100. With the instructions now not visible, the user is again supposed to intuitively know to take the third graspable end 413 in a sixth direction 416, thereby stretching out the prior art equipment drape 100.

Figure 6:
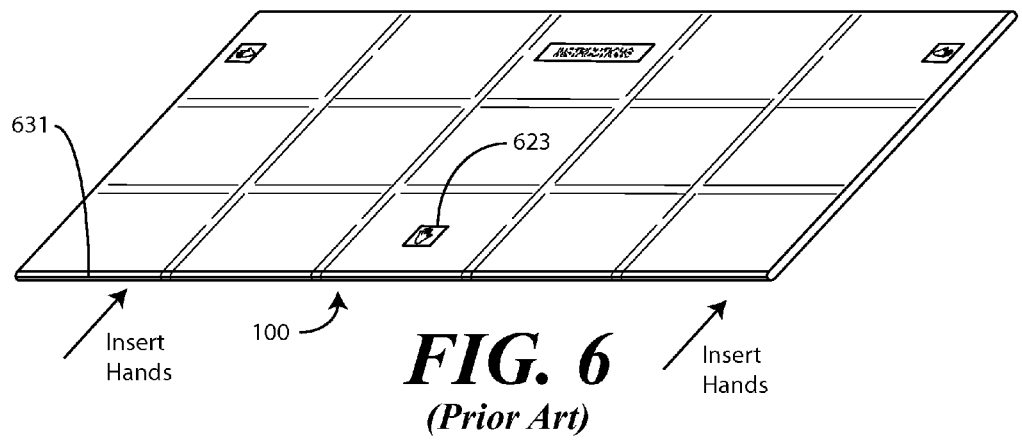

Note that the steps of FIGS. 5 and 6 are counterintuitive relative to the stickers 121,221. The stickers 121,221 shown in FIGS. 5 and 6 suggest that the first graspable end 111 and second graspable end 112 should still be grasped. However, this is not the case. If the first graspable end 111 and second graspable end 112 are indeed grasped, the prior art equipment drape cannot be unfolded further. This makes little sense, but that is the way that it is.

Turning now to FIG. 6, illustrated therein is the prior art equipment drape 100 when completely unfolded as described in FIGS. 1-5. At this point, there is a third hand sticker 623. The third hand sticker 623 is shown as being blurry because it is actually visible only through several layers 631 of the prior art equipment drape 100. The user must then sort through the several layers 631, determine which of the several layers 631 includes the third hand sticker 623, and then insert their hands between this layer and the one just above.

Figure 7:
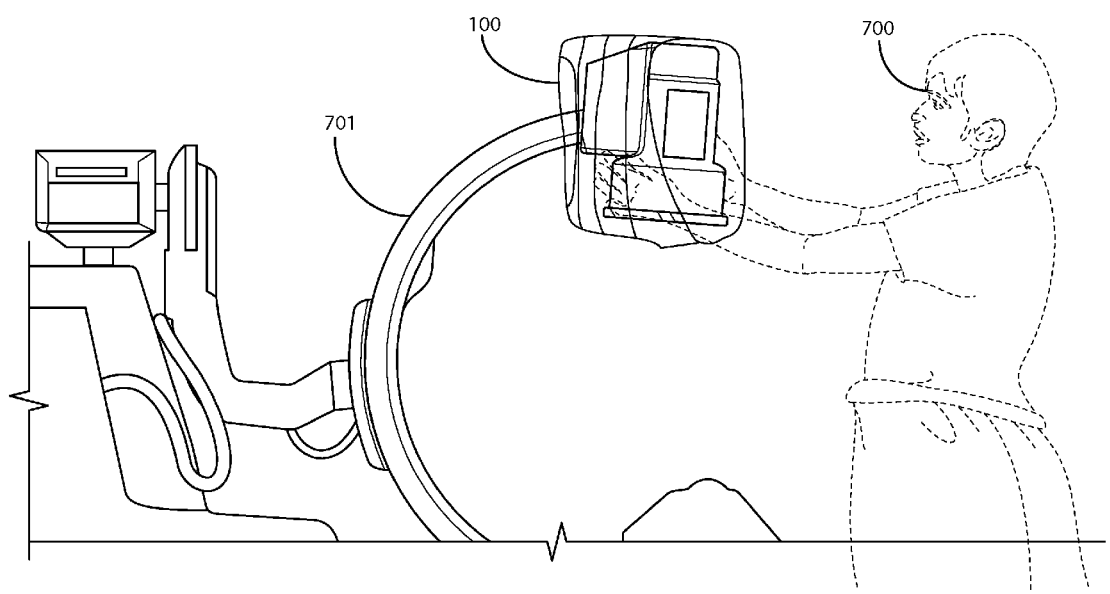
FIGS. 7-9 illustrate a prior art equipment drape being deployed on equipment.
Figure 8:
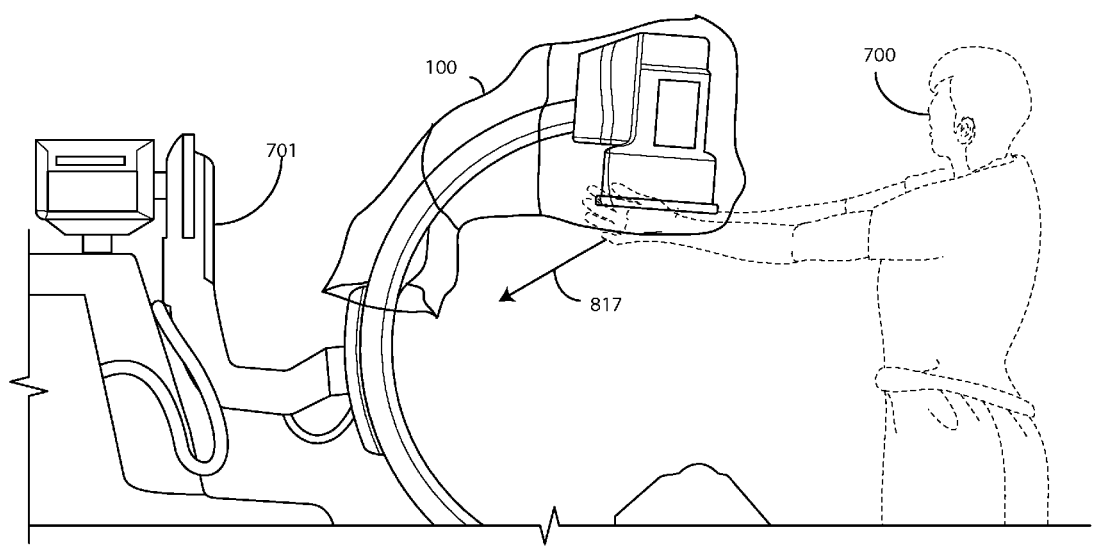
Figure 9:
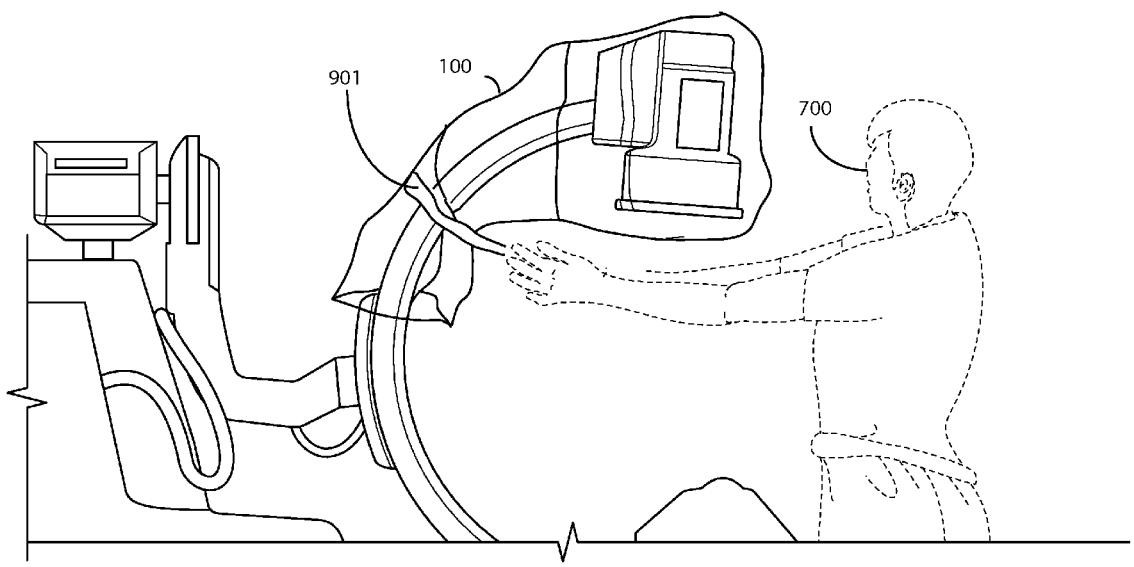

Once this is complete, turning now to FIG. 7 the user 700 begins to place the prior art equipment drape 100 over a piece of equipment 701. Turning now to FIG. 8, the user 700 then begins to move the hands in a seventh motion 817 along the piece of equipment 701, thereby expanding the prior art equipment drape 100. Turning to FIG. 9, the user 700 may then optionally tie off the prior art equipment drape 100 with a tie 901.

As shown above, the prior art equipment drape 100 takes a minimum of ten grasping and moving steps before the prior art equipment drape 100 can be applied to the piece of equipment (701) as shown in FIG. 7. Turning now to FIGS. 10-13, illustrated therein is one embodiment of an equipment drape 1000 configured in accordance with embodiments of the present invention. This equipment drape 1000 can be applied to a piece of equipment in as little as three steps. This results in a 70% efficiency increase in its deployment.

Figure 10:
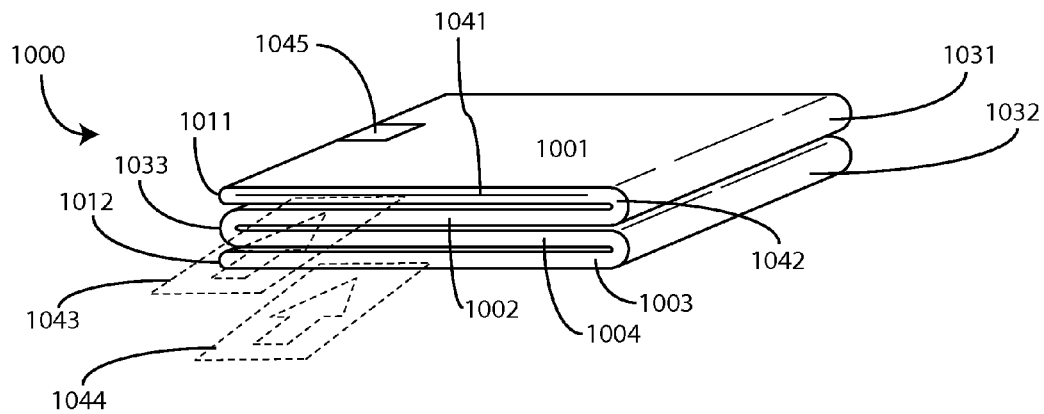
FIG. 10 illustrates one embodiment of an equipment drape configured in accordance with embodiments of the invention.

Turning first to FIG. 10, illustrated therein is the equipment drape 1000 folded in an accordion fold. Specifically, a first section 1001 is folded relative to a second section 1002 along a first longitudinal fold 1031. Similarly, a third section 1003 is folded relative to a fourth section 1004 along a second longitudinal fold 1032. These sections are then folded, in the opposite direction, along a third longitudinal fold 1033. Thus, the first section 1001, second section 1002, third section 1003, and fourth section 1004 are folded in an accordion fashion. Where three folds are used, this can be referred to as a "reverse book fold" with the first section 1001 and second section 1002 forming a first portion of the book and the third section 1003 and fourth section 1004 forming the second portion of the book. First fold 1031 and second fold 1032 are in opposite directions relative to the third fold 1033, hence the reverse book name.

In one embodiment, to prevent the "book" from opening at the "spine," an adhesive layer 1045 can be added. In one embodiment, the adhesive layer 1045 is attached to a first distal end 1011 and a second distal end 1012 such that it wraps about the "spine" of the book. As will be shown in subsequent figures, during manufacture the first distal end 1011 and second distal end 1012 are folded along the first fold 1031 and second fold 1032 such that they meet at a longitudinal part. In the illustrative embodiment of FIG. 10, the longitudinal part runs down the spine of the book. As such, the adhesive layer 1045 spans the longitudinal part and keeps the spine from unfolding until the equipment drape 1000 is ready for use.

In one embodiment, the adhesive layer 1045 can be as simple as a layer of tape. In one embodiment, the tape can include a removable adhesive such that the adhesive layer 1045 can be easily removed from the two distal ends 1011, 1012. As the adhesive layer is generally very small, it is not always necessary to remove it before using the equipment drape 1000 on a piece of equipment. In such situations, a perforation can be placed along the longitudinal part to make separating the first section 1001 and the third section 1003 easy during deployment.

In one embodiment, the equipment drape 1000 has an elongated drape body that is generally closed at one end and includes an equipment opening 1041 at the other, distal end. As shown in FIG. 10, the equipment opening 1041 is disposed along a first edge 1042 of the folded equipment drape 1000.

As an option to assist users in opening the equipment drape 1000, in one embodiment two insertion indicators 1043,1044 can be included. In one embodiment the two insertion indicators 1043,1044 are attached by way of a removable adhesive to the elongated drape body along the equipment opening 1041. Removable adhesive is a good option for an attachment mechanism so that the insertion indicators 1043,1044 can be removed after the equipment drape 1000 has been placed over the piece of equipment. This prevents the insertion indicators 1043,1044 from interfering with imaging when the piece of equipment is an imaging device.

In one embodiment, the insertion indicators 1043,1044 can be manufactured from paper or a similar material. Experimental testing has shown that a stiffer material than conventional typing paper, such as card stock or cardboard, can assist users in more quickly locating the layer of the equipment cover 1000 to which they are attached.

As shown in FIG. 10, the insertion indicators 1043,1044 extend outward from the folded equipment drape 1000. In the illustrative embodiment of FIG. 10, the insertion indicators 1043,1044 extend outward from the first edge 1042. In such a configuration, they can be easily located. Further, users can determine exactly where to insert their hands prior to any unfolding steps.

To deploy the equipment drape 1000, a user simply inserts their hands in accordance with the insertion indicators 1043, 1044. In one embodiment, the insertion indicators 1043,1044 have arrows on them to show where the hands should be inserted. The user may use the insertion indicators 1043,1044 to aid in hand insertion by placing their hands along the insertion indicators 1043,1044 and sliding them in the direction of the printed arrows. Once the hands are inserted, the deployment can begin.

Figure 11:
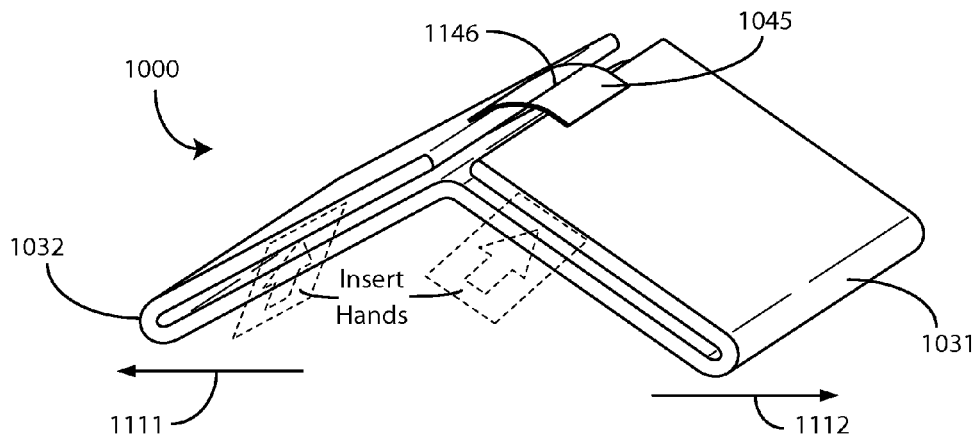
FIG. 11 illustrates one embodiment of an equipment drape configured in accordance with embodiments of the invention being deployed.

Turning now to FIG. 11, illustrated therein is the second step of deployment of the equipment drape 1000. With the hands inserted, the user simply spreads the hands apart, with one hand moving in a first direction 1111 and the other hand moving in a second direction 1112. This separates the first fold 1031 from the second fold 1032, thereby "opening" the book.

Where an adhesive layer 1045 is included with a perforation 1146, the user simply breaks the perforation by continuing to move the hands in the first direction 1111 and second direction 1112. This separates the two distal ends 1011,1012. Alternatively, turning to FIG. 11, the perforation 1146 can be torn by moving the hands in directions 1211,1212.

Figure 12:
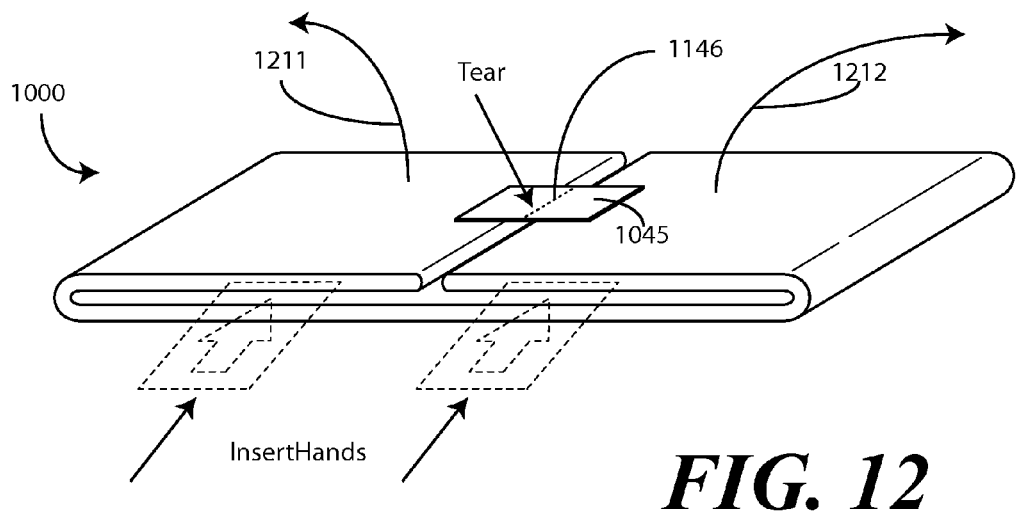
FIG. 12 illustrates one embodiment of an equipment drape configured in accordance with embodiments of the invention being deployed.

Turning now to FIG. 12, as the user continues moving in the first direction (1111) and second direction (1112), the book unfolds. The user then moves the hands in third direction 1211 and fourth direction 1212, which are minor variations from the first direction (1111) and the second direction (1112). If the adhesive layer 1045 was not torn with the motion shown in FIG. 11, the motion along the third direction 1211 and fourth direction 1212 will cause the perforation 1146 to tear. Alternatively, where a perforation 1146 is not included, removable adhesive can be used in conjunction with the adhesive layer 1045. In such a scenario, motion by the user's hands in the third direction 1211 and fourth direction 1212 will cause the removable adhesive to separate from the equipment drape 1000.

Figure 13:
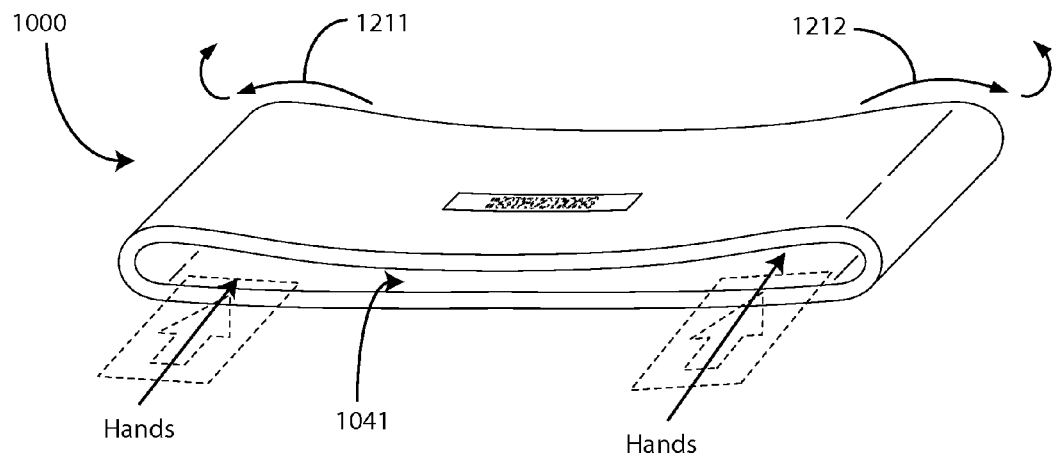
FIG. 13 illustrates one embodiment of an equipment drape configured in accordance with embodiments of the invention being deployed.

Turning now to FIG. 13, illustrated therein is the equipment drape 1000 after the user's hands have continued to move in the third direction 1211 and fourth direction 1212. As shown, the equipment drape 1000 has expanded with the equipment opening 1041 expanding. The user can then place the equipment opening 1041 over the appropriate piece of equipment as shown in FIG. 7. Thus, as shown, the number of steps required to deploy the equipment drape 1000 has been dramatically reduced when compared to the prior art.

Figure 14:
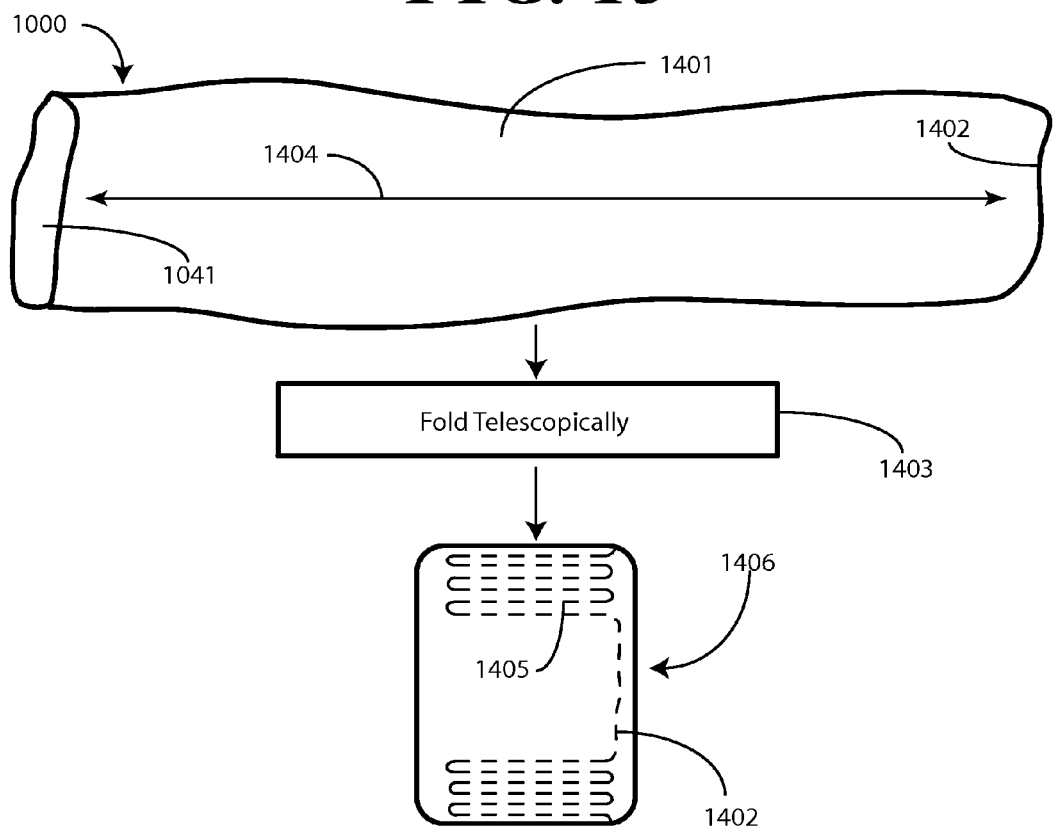
FIG. 14 illustrates a method of configuring an equipment drape in accordance with embodiments of the invention.
Figure 15:
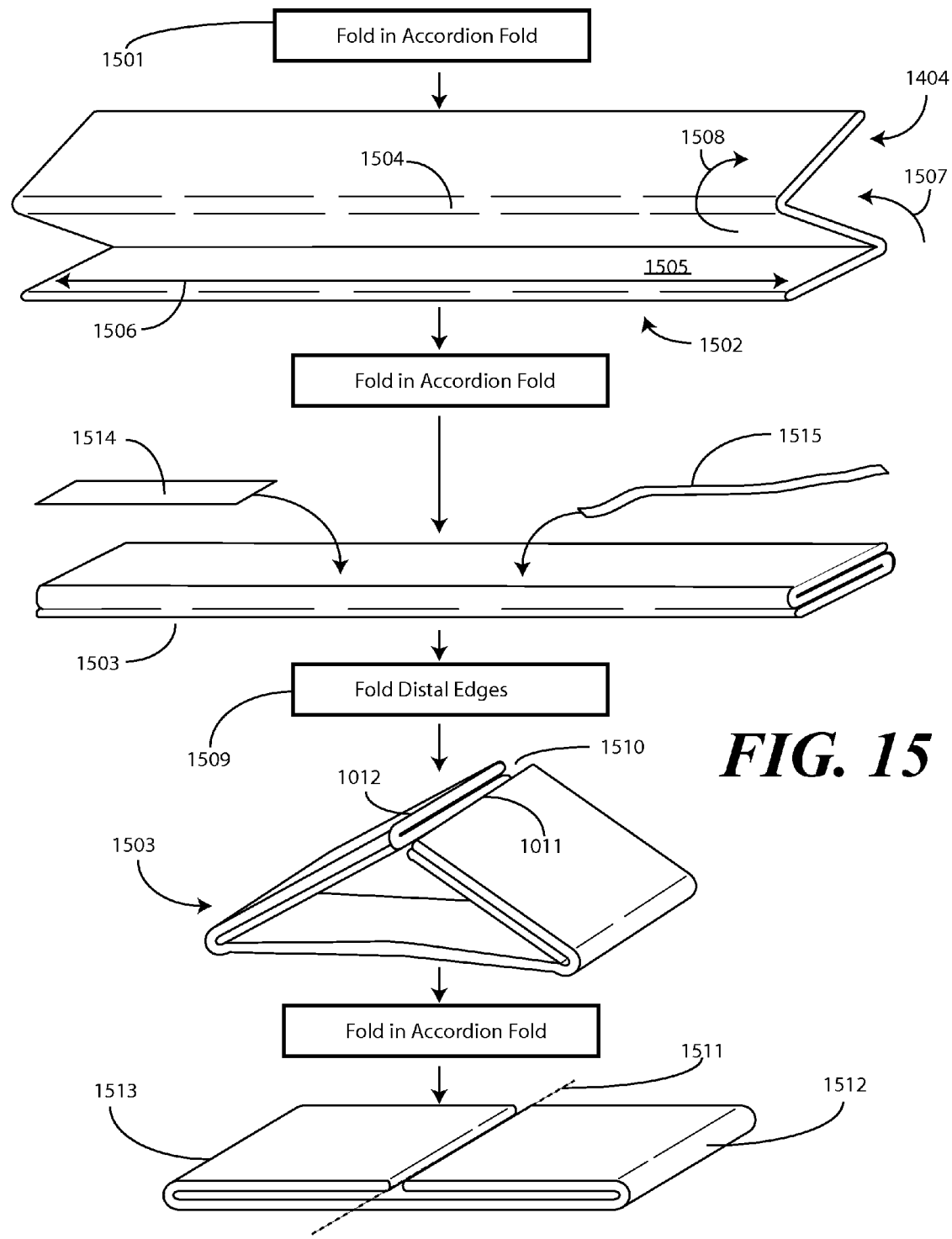
FIG. 15 illustrates a method of configuring an equipment drape in accordance with embodiments of the invention.
Figure 16:
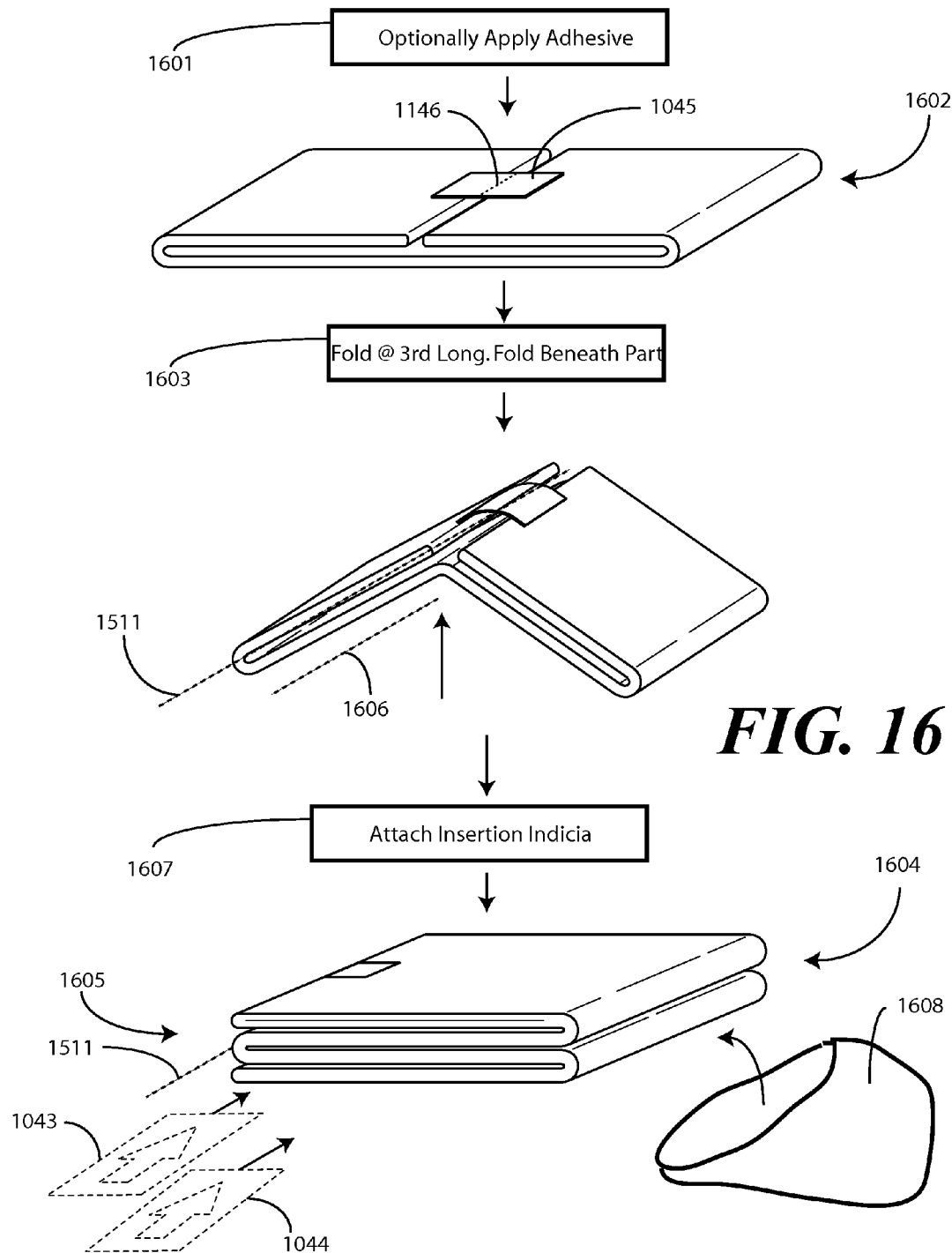
FIG. 16 illustrates a method of configuring an equipment drape in accordance with embodiments of the invention.

Now that deployment of the equipment drape 1000 has been shown, the manufacturing method will be shown. Turning now to FIGS. 14-16, illustrated therein is one method, shown graphically, of manufacturing an equipment drape 1000 in accordance with embodiments of the invention. Embodiments of the invention can be manufactured with the assistance of automated folding machines in an automated process. Such machines, which will be obvious to those of ordinary skill in the art having the benefit of this disclosure, will include infeed sections, folding sections, tucking sections, and packaging sections. Platen surfaces, belt fed devices, rollers which roll on underlying tracks and may be driven by pistons, folding arms, guide rods, conveyors, and electronic control devices can be configured to carry out the steps shown in these figures.

Beginning with FIG. 14, an elongated drape body 1401 defines the equipment opening 1041 and terminates, in one embodiment, at a distal end 1402. In one embodiment, the elongated drape body 1401 is transparent, although embodiments of the invention are not so limited. Opaque materials can be used as well.

The equipment drape 1000 is shown illustratively in FIG. 14 as being tubular for simplicity. However, it will be clear to those of ordinary skill in the art having the benefit of this disclosure that embodiments of the invention are not so limited. The elongated drape body 1401, for example, can include contours and shapes so as to fit more snuggly over a particular piece of equipment. Additionally, multiple equipment openings can be provided, and the distal end 1402 can be left open.

The elongated drape body 1401 is then folded telescopically 1403 along a length 1404 to form a telescopic equipment drape 1406 or telescopic drape body. The telescopic folds 1405 are shown as dashed lines in FIG. 14.

Turning now to FIG. 15, the telescopic equipment drape 1404 is then folded 1501 in an accordion fold to form 1502 a rectangular shape 1503. In this illustrative embodiment, the accordion fold is formed with a plurality of lateral folds. The lateral folds of FIG. 15 comprise two folds 1504,1505 disposed across a width 1506 of the telescopic equipment drape 1404. The two folds 1504,1505 move in opposite directions 1507,1508, thereby imparting the accordion style fold to the rectangular shape 1503.

If instructions 1514 are desired, the instructions 1514 comprising an instructional guide can be coupled to the elongated drape body at this time. As will be described below, in one embodiment, the instructions 1514 will be disposed therealong so as to span the longitudinal part 1511 that will be formed. In this configuration, the instructions 1514 will be visible with the distal edges 1011,1012 are unfolded, as was shown above in FIG. 13.

In one embodiment, optional equipment ties 1515 can be adhesively and detachably coupled to the equipment drape. Some applications require that the drape be tied to the machine to ensure that it stays wrapped about the machine. To make this process easier, detachable equipment ties 1515 can be included with the drape.

The distal edges 1011,1012 of the rectangular shape 1503 are then folded 1509 back over the rectangular shape 1503 until the two distal edges 1011,1012 meet 1510 at a longitudinal part 1511. This is accomplished by making two longitudinal folds 1512,1513 disposed along the width 1506 of the telescopically folded equipment drape 1404, as shown at the bottom of FIG. 15.

Turning now to FIG. 16, an adhesive layer 1045 can optionally be applied at step 1601. As noted above, the adhesive layer 1045 may also include a perforation 1146 as well. In one embodiment, the adhesive layer 1045 spans the longitudinal part 1511. Where a perforation 1146 is used, it can be substantially aligned with the longitudinal part 1511.

The reduced rectangular shape 1602 can then be folded 1603 in half beneath the longitudinal part 1511 such that the longitudinal part 1511 is disposed at an edge 1605 of the resulting folded equipment drape 1604. This is accomplished by applying a third longitudinal fold 1606 beneath the longitudinal part 1511. The third longitudinal fold 1606 is opposite in direction from the first longitudinal fold (1512) and second longitudinal fold (1513) in the illustrative embodiment of FIG. 16. Where the adhesive layer 1045 is used, the adhesive layer 1045 will traverse a convex side of the longitudinal fold 1606 when the fold is completed.

At this time, insertion indicators 1043,1044 can be attached to the equipment drape. In one embodiment, the insertion indicators 1043,1044 comprise tags having arrows disposed thereon. These insertion indicators 1043,1044 instruct a user where to insert their hands into the telescopic fold (1405), and in one embodiment can be attached to the equipment opening 1041. Note that the insertion indicators 1043,1044 could be attached at various steps of the process, including prior to making the telescopic fold (1405), or prior to making the accordion fold. The drape can be packaged by disposing a packaging bag 1608 about the folded drape.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. An equipment drape, comprising:
    an elongated drape body defining an equipment opening and comprising a telescopic fold along a length thereof to form a telescopic drape body; and
    two or fewer insertion indicators disposed along the equipment opening;
    wherein the telescopic drape body comprises an accordion fold along a width so as to be substantially a rectangular shape;
    wherein distal edges of the rectangular shape are folded back across the rectangular shape to meet at a longitudinal part;
    wherein the rectangular shape is folded on a longitudinal fold line beneath the longitudinal part to form a folded equipment drape having the longitudinal part disposed along a first edge thereof and the two or fewer insertion indicators disposed along a second edge thereof.

2. The equipment drape of claim 1, further comprising an adhesive layer coupled to each of the distal edges and spanning the longitudinal part.

3. The equipment drape of claim 2, wherein the adhesive layer comprises a perforation.

4. The equipment drape of claim 3, wherein the perforation is substantially aligned with the longitudinal part.

5. The equipment drape of claim 1, further comprising an instructional guide coupled to the elongated drape body and spanning the longitudinal part so as to be visible when the distal edges are unfolded.

6. The equipment drape of claim 1, wherein the two or fewer insertion indicators comprise tags adhesively coupled to the elongated drape body along the equipment opening.

7. The equipment drape of claim 6, wherein each of the two or fewer insertion indicators comprises arrows disposed thereon.

8. The equipment drape of claim 7, wherein the arrows are configured to instruct a user where to insert their hands to unfold the telescopic fold.

9. The equipment drape of claim 1, wherein the elongated drape body is transparent and closed at an end disposed distally from the equipment opening.

10. The equipment drape of claim 1, wherein the accordion fold comprises a first fold and a second fold.

11. The equipment drape of claim 1, wherein the longitudinal part is medially disposed along the rectangular shape.

12. A method of folding an equipment drape, comprising:
folding the equipment drape telescopically along a length to form a telescopic equipment drape;
folding the telescopic equipment drape in an accordion fold to form a rectangular shape;
folding two distal edges of the rectangular shape back over the rectangular shape until the two distal edges meet at a longitudinal part;
and folding the rectangular shape in half beneath the longitudinal part such that the longitudinal part is disposed at an edge of a resulting folded equipment drape.

13. The method of claim 12, further comprising attaching two or fewer insertion indicators to the equipment drape.

14. The method of claim 12, further comprising attaching an adhesive layer to the two distal edges prior to the folding the rectangular shape in half.

15. The method of claim 12, further comprising attaching instructions to the equipment drape.

16. A folded equipment drape, comprising:
an elongated drape body folded telescopically along its length to form a telescopically folded equipment drape;
a plurality of lateral folds comprising an accordion fold disposed along a length of the telescopically folded equipment drape; and
a plurality of longitudinal folds disposed along a width of the telescopically folded equipment drape;
wherein distal edges of the telescopically folded equipment drape are folded back across the width at two longitudinal folds to meet at a third longitudinal fold;
wherein the third longitudinal fold is opposite in direction from the two longitudinal folds.

17. The telescopically folded equipment drape of claim 16, further comprising insertion labels disposed on the telescopically folded equipment drape.

18. The telescopically folded equipment drape of claim 16, further comprising equipment ties adhesively and detachably coupled to the telescopically folded equipment drape.

19. The telescopically folded equipment drape of claim 16, further comprising a perforated adhesive binder coupled to the distal edges and spanning the third longitudinal fold so as to traverse a convex side of the third longitudinal fold.

20. The telescopically folded equipment drape of claim 16, further comprising a packaging bag disposed about the telescopically folded equipment drape so as to seal the telescopically folded equipment drape therein.

\* \* \* \* \*